United States Patent [19]

Martini et al.

[11] Patent Number: 5,712,260
[45] Date of Patent: Jan. 27, 1998

[54] ESTRAMUSTINE FORMULATIONS WITH IMPROVED PHARMACEUTICAL PROPERTIES

[75] Inventors: Alessandro Martini, Milan; Giuseppe Maccari, Voghera; Lorena Muggetti, Milan; Giuseppe Colombo, Milan; Giovanni Buzzi, Milan, all of Italy

[73] Assignee: Pharmacia AB, Stockholm, Sweden

[21] Appl. No.: 635,956

[22] PCT Filed: Sep. 1, 1995

[86] PCT No.: PCT/EP95/03438

§ 371 Date: May 6, 1996

§ 102(e) Date: May 6, 1996

[87] PCT Pub. No.: WO96/09072

PCT Pub. Date: Mar. 28, 1996

[30] Foreign Application Priority Data

Sep. 22, 1994 [GB] United Kingdom ............... 9419153.3

[51] Int. Cl.$^6$ ............................................. A61K 31/705
[52] U.S. Cl. ........................ 514/58; 514/169; 514/182; 514/777
[58] Field of Search ........................ 514/58, 182, 951, 514/169, 777

[56] References Cited

U.S. PATENT DOCUMENTS 3,299,104 1/1967 Fex ............................... 360/397.4
5,126,333 6/1992 Martini et al. ..................... 514/58

FOREIGN PATENT DOCUMENTS 0351561 1/1990 European Pat. Off. .
0477107 3/1992 European Pat. Off. .

OTHER PUBLICATIONS

Cserhati, Tibor. *Biomed. Chromat.*, vol. 8(6): 267–272, (1994).
Cserhati, Tibor. *Fresnius J. Anal. Chem.*, vol. 349(10–11): 751–755, (1994).

Loftsson et al. *Int. J. Pharm.*, vol. 79(2–3): 107–112, (1992).
Cserhati, Tibor. *Int. J. Pharm.*, vol. 108(1): 69–75, (1994).

*Primary Examiner*—John Kight
*Assistant Examiner*—Howard C. Lee
*Attorney, Agent, or Firm*—Oblon, Spivak, McClelland, Maier & Neustadt, P.C.

[57] ABSTRACT

The present invention provides a pharmaceutical composition comprising an estramustine derivative and a cyclodextrin, particularly in the manufacture of a medicament suitable for the oral administration of an estramustine derivative to a patient suffering from a tumor.

Estramustine derivatives according to the invention are, for example, compounds of general formula (I)

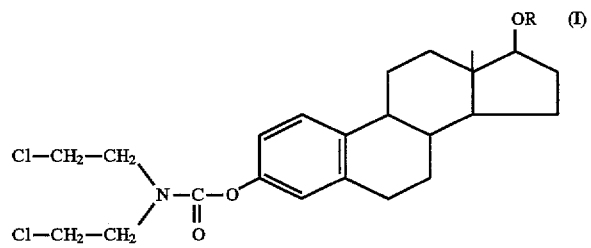

wherein R is

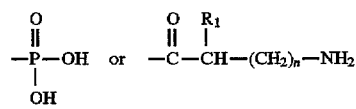

in which $R_1$ is $C_1$–$C_4$ alkyl and n is 0, 1 or 2, and the pharmaceutically acceptable salts thereof.

13 Claims, No Drawings

ESTRAMUSTINE FORMULATIONS WITH IMPROVED PHARMACEUTICAL PROPERTIES

The present invention relates to pharmaceutical compositions comprising an estramustine derivative and a cyclodextrin. Cyclodextrins (hereinafter CD) are well known cyclic oligosaccharides, made up of D-glucose residues, having a cylindrical cavity shaped structure capable of including various guest molecules. Indeed, one of the most interesting properties of CD is their ability to form inclusion compounds or complexes. This interaction greatly depends on the hydrophobicity of the guest molecule, the steric hindrance between the drug and the CD, and the size of the CD cavity. Anyway, this kind of complexation confers new physicochemical properties to the drugs, and is extensively used in the pharmaceutical field to improve the solubility and stability of active drug substances [O. Bekers et al., Drug Dev. Ind. Pharm., 17, 1503 (1991); J. Szejtli, Pharm. Tech. Int., February 1991, 15] and, as a consequence, their dissolution characteristics and bioavailability.

More generally, the drug-CD complexation is used to improve the bioavailability of active molecules presenting a very low water solubility but a good absorption rate through biological membranes [D. Duchene et al., STP Pharma, 323 (1985)]. Said inclusion complexes are usually prepared in a liquid medium, and then, upon drying they are obtained in powder form.

Various methods for preparing solid inclusion compounds, such as kneading [K. Uekama et al., Int. J. Pharm., 10, 1 (1982)], co-precipitation [K. Uekama et al., Int. J. Pharm., 16, 327 (1983)], spray-drying [H. P. R. Bootsma et al., Int. J. Pharm., 51, 213 (1989)], freeze-drying [P. Chiesi et al., U.S. Pat. No. 4,603,123, Jul. 29 (1986)] are suitable.

In some cases the formation of the complex in the solid phase is thermodynamically spontaneous and inclusion could be normally achieved by grinding [C. Torricelli et al., Int. J. Pharm., 71, 19 (1991)].

We have now surprisingly found that the bioavailibility characteristics of certain drugs can be still improved with CD also for molecules with high water solubility, that theoretically do not need any particular formulation approach specifically intended for improving their solubility or their rate of dissolution from a therapeutic dosage form.

The present invention relates to pharmaceutical composition comprising an estramustine derivative and a cyclodextrin.

Estramustine derivatives according to the invention are, for example, the compounds of formula (I):

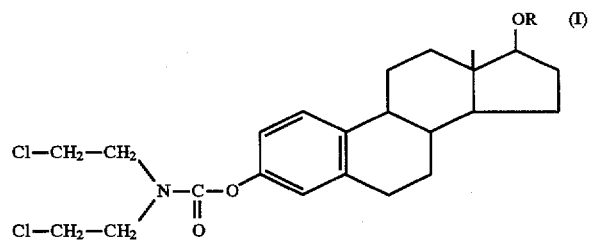

wherein R is

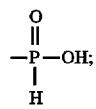

in which $R_1$ is $C_1$–$C_4$ alkyl and n is 0, 1 or 2, and the pharmaceutically acceptable salts thereof.

Particularly preferred estramustine derivatives are the compounds of formula (I) wherein R is

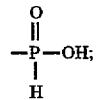

i.e. Estramustine-17-phosphate, and its disodium salt, i.e. Estramustine-17-disodium phosphate; or wherein R is

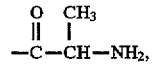

i.e. Estramustine-17-L-alaninate, and its methansulfonate salt, i.e. Estramustine-17-L-alaninate methan-sulfonate.

Estramustine-17-phosphate disodium salt (GB patent 1016959) is a drug used in prostatic cancer therapy, most widely in the treatment of patients who can no longer be treated with hormones and patients with a poor prognosis. The drug is used above all by patients in whom the illness has spread through metastatic tumors. Since the size of the tumor is reduced, the pain caused by the cancer is also relieved. Although effective in therapy and absorbable through the gastrointestinal wall, Estramustine-17-phosphate disodium salt has strong limitations in the oral administration due to its interaction with foods and drinks: it is necessary to administer the drug in fasting condition in order to avoid the reprecipitation of the drug that is induced by cations and in particular by calcium ions [P. O. Gunnarsson et al., Europ. J. Clin. Pharmac., 38, 189 (1990)].

This fact dramatically reduces the bioavailibility of the drug and induces gastrointestinal side effects.

Estramustine-17-L-alaninate (patent application EP351561) has the same therapeutic indications as Estramustine-17-phosphate disodium salt and quite the same trouble of reprecipitation, although induced by anionic species, such as chlorine ions. The present invention generally refers to the use of any CD, natural ($\alpha$-CD, $\beta$-CD and $\gamma$-CD), synthetic or semi-synthetic (as for example hydroxypropyl-$\beta$-CD or dimethyl-$\beta$-CD) or dehydrated [A. Martini et al., U.S. Pat. No. 5,126,333, Jun. 30 (1992)]. In particular, preferred cyclodextrins are $\beta$-cyclodextrin, hydroxypropyl-$\beta$-cyclodextrin and $\gamma$-cyclodextrin.

What we surprisingly found is that when cyclodextrins are mixed with Estramustine-17-phosphate disodium salt, the solubility of the drug itself does not change in a significant way, but the effects of reprecipitation induced by cations on the drug are quite negligible, since cyclodextrins are able to mask the site of interaction of Estramustine-17-phosphate with calcium or other cations.

The formation of a complex in solution between the drug and an appropriate cyclodextrin can avoid the reprecipitation of the free drug or of a salt of the drug in physiological conditions. This phenomenon can offer a Big advantage in the administration of the drug rendering its bioavailability higher regardless of fasting/non-fasting conditions.

Cyclodextrins are surprisingly able not only to avoid the reprecipitation of Estramustine-17-phosphate in the presence of cations, but also to permit the passage in solution of the drug when, as example, calcium ions are present in the dissolution medium and to redissolve the already formed precipitate of Estramustine-17-phosphate with calcium.

Cyclodextrins have also been shown to interact with Estramustine-17-L-alaninate avoiding any effect of reprecipitation by anionic species.

Moreover, we have noticed that, for this application, it is not necessary to form the complex between drug and cyclodextrin in the solid state, but it is sufficient to administer a simple physical mixture of the two chemical entities.

The proportion between the drug substance and the cyclodextrin may vary, e.g. from 1:0.5 to 1:10 (molar ratio). A preferred molar ratio is from 1:1 to 1:4. A suitable range is from 1:1 to 1:2.

A pharmaceutical formulation containing the drug-cyclodextrin composition of the invention, which is included within the scope of the invention, can be prepared following known and conventional procedures. The drug-cyclodextrin system according to the invention can be used to prepare solid, semi-solid or liquid formulations for oral dosage forms, e.g. tablets, hard or soft gelatine capsules, sachets and so on, with or without the addition of one or more of the excipients commonly used in pharmaceutical formulations. Pharmaceutically acceptable carriers or diluents may be present.

The dosage depends on the age, weight, conditions of the patient and administration route. For example the dosage adopted for oral administration for humans is from 50 to 1,500 mg daily.

The present invention also provides a pharmaceutical composition as defined above for use in a method of treatment of the human or animal body by therapy, in particular for treatment of a tumor.

The present invention also provides the use of a cyclodextrin in the manufacture of a medicament suitable for the oral administration of an estramustine derivative to a patient, said medicament comprising an estramustine derivative and the cyclodextrin, and the use of a cyclodextrin in the manufacture of a medicament for the treatment of a tumor, said medicament comprising an estramustine derivative and the cyclodextrin. The composition of the present invention may be used in a method for treating or preventing a tumor which comprises administering to a subject suffering therefrom or liable to suffer therefrom an effective amount of the composition.

The following examples are only given with the purpose of better illustrating the invention but in no way they must be considered as a limitation of the scope of the invention itself.

EXAMPLE 1

To a solution in a pH 3.1 HCl/KCl buffer (I=0.1), containing 640 mcg/ml of Estramustine-17-phosphate disodium salt (EPS), were added appropriate quantities of calcium chloride in order to have drug:salt molar ratios in the range from 1:0 to 1:1. The samples were filtered and the quantity of Estramustine-17-phosphate sodium salt in solution was assayed by UV spectroscopy.

The results are shown in Table 1.

TABLE 1

| $EPS:CaCl_2$ molar ratios | EPS in solution |
|---|---|
| 1:0 | 100% |
| 1:0.25 | 42% |
| 1:0.5 | 21% |
| 1:1 | 14% |

EXAMPLE 2

To a solution in a pH 3.1 HCl/KCl buffer (I=0.1), containing about 1 mg/ml of Estramustine-17-phosphate disodium salt (EPS) and different quantities of cyclodextrins: β-cyclodextrin (β-CD), 2-hydroxypropyl-β-cyclodextrin (HP-β-CD) or γ-cyclodextrin (γ-CD), were added appropriate quantities of calcium chloride in order to have a drug:salt molar ratio of 1:1. The samples were filtered and the quantity of Estramustine-17-phosphate disodium salt in solution was assayed by UV spectroscopy. The results are shown in Tables 2a, 2b and 2c.

TABLE 2a

| $EPS:β-CD:CaCl_2$ molar ratios | EPS in solution |
|---|---|
| 1:0:1 | 16% |
| 1:1:1 | 52% |
| 1:2:1 | 90% |
| 1:3:1 | 100% |
| 1:4:1 | 100% |

TABLE 2b

| $EPS:HP-β-CD:CaCl_2$ molar ratios | EPS in solution |
|---|---|
| 1:0:1 | 16% |
| 1:1:1 | 54% |
| 1:2:1 | 78% |
| 1:3:1 | 100% |
| 1:4:1 | 100% |

TABLE 2c

| $EPS:γ-CD:CaCl_2$ molar ratios | EPS in solution |
|---|---|
| 1:0:1 | 16% |
| 1:1:1 | 52% |
| 1:2:1 | 87% |
| 1:3:1 | 100% |
| 1:4:1 | 100% |

EXAMPLE 3

To a solution in a pH 3.1 HCl/KCl buffer (I=0.1), containing about 1 mg/ml of Estramustine-17-phosphate disodium salt (EPS) and different quantities of cyclodextrins: β-cyclodextrin (β-CD), 2-hydroxypropyl-β-cyclodextrin (HP-β-CD) or γ-cyclodextrin (γ-CD), were added appropriate quantities of calcium chloride in order to have a drug:salt molar ratio of 1:2. The samples were filtered and the quantity of Estramustine-17-phosphate disodium salt in solution was assayed by UV spectroscopy. The results are shown in Tables 3a, 3b and 3c.

TABLE 3a

| EPS:β-CD:CaCl₂ molar ratios | EPS in solution |
|---|---|
| 1:0:2 | 4% |
| 1:1:2 | 51% |
| 1:2:2 | 86% |
| 1:3:2 | 100% |
| 1:4:2 | 100% |

TABLE 3b

| EPS:HP-β-CD:CaCl₂ molar ratios | EPS in solution |
|---|---|
| 1:0:2 | 4% |
| 1:1:2 | 57% |
| 1:2:2 | 77% |
| 1:3:2 | 100% |
| 1:4:2 | 100% |

TABLE 3c

| EPS:γ-CD:CaCl₂ molar ratios | EPS in solution |
|---|---|
| 1:0:2 | 4% |
| 1:1:2 | 39% |
| 1:2:2 | 56% |
| 1:3:2 | 96% |
| 1:4:2 | 98% |

EXAMPLE 4

To a solution in a pH 3.1 HCl/KCl buffer (I=0.1), containing about 1 mg/ml of Estramustine-17-phosphate disodium salt (EPS) and different quantities of cyclodextrins: β-cyclodextrin (β-CD), or 2-hydroxypropyl-β-cyclodextrin (HP-β-CD) or γ-cyclodextrin (γ-CD), were added appropriate quantities of calcium chloride in order to have a drug:salt molar ratio of 1:4. The samples were filtered and the quantity of Estramustine-17-phosphate disodium salt in solution was assayed by UV spectroscopy.

The results are shown in Tables 4a, 4b and 4c.

TABLE 4a

| EPS:β-CD:CaCl₂ molar ratios | EPS in solution |
|---|---|
| 1:0:4 | 4% |
| 1:1:4 | 48% |
| 1:2:4 | 81% |
| 1:3:4 | 100% |
| 1:4:4 | 100% |

TABLE 4b

| EPS:HP-β-CD:CaCl₂ molar ratios | EPS in solution |
|---|---|
| 1:0:4 | 4% |
| 1:1:4 | 49% |
| 1:2:4 | 61% |
| 1:3:4 | 77% |
| 1:4:4 | 100% |

TABLE 4c

| EPS:γ-CD:CaCl₂ molar ratios | EPS in solution |
|---|---|
| 1:0:4 | 4% |
| 1:1:4 | 30% |
| 1:2:4 | 65% |
| 1:3:4 | 92% |
| 1:4:4 | 100% |

EXAMPLE 5

To a solution in a pH 3.1 HCl/KCl buffer (I=0.1), containing about 1 mg/ml of Estramustine-17-phosphate disodium salt (EPS) and 1 mole of calcium chloride per mole of EPS, were added different quantities of cyclodextrins: β-cyclodextrin (β-CD), or 2-hydroxypropyl-β-cyclodextrin (HP-β-CD) or γ-cyclodextrin (γ-CD), in order to have drug:cyclodextrin molar ratios from 1:0 to 1:4 for evaluating the solubilization properties of cyclodextrins in dissolving a previously formed precipitate of EPS with calcium. The samples were filtered and the quantity of Estramustine disodium salt in solution was assayed by UV spectroscopy.

The results are shown in Tables 5a, 5b and 5c.

TABLE 5a

| EPS:CaCl₂:β-CD molar ratios | EPS in solution |
|---|---|
| 1:1:0 | 16% |
| 1:1:2 | 77% |
| 1:1:3 | 83% |
| 1:1:4 | 95% |

TABLE 5b

| EPS:CaCl₂:HP-β-CD molar ratios | EPS in solution |
|---|---|
| 1:1:0 | 16% |
| 1:1:2 | 65% |
| 1:1:3 | 67% |
| 1:1:4 | 73% |

TABLE 5c

| EPS:CaCl₂:γ-CD molar ratios | EPS in solution |
|---|---|
| 1:1:0 | 16% |
| 1:1:2 | 64% |
| 1:1:3 | 68% |
| 1:1:4 | 75% |

EXAMPLE 6

To a solution in a pH 3.1 HCl/KCl buffer (I=0.1), containing about 1 mg/ml of Estramustine-17-phosphate disodium salt (EPS) and 2 mole of calcium chloride per mole of EPS, were added different quantities of cyclodextrins: β-cyclodextrin (β-CD), 2-hydroxypropyl-β-cyclodextrin (HP-β-CD) or γ-cyclodextrin (γ-CD), in order to have drug:cyclodextrin molar ratios from 1:0 to 1:4 for evaluating the solubilization properties of cyclodextrins in dissolving a previously formed precipitate of EPS with calcium. The samples were filtered and the quantity of Estramustine-17-phosphate disodium salt in solution was assayed by UV spectroscopy.

The results are shown in Tables 6a, 6b and 6c.

TABLE 6a

| EPS:CaCl$_2$:β-CD molar ratios | EPS in solution |
|---|---|
| 1:2:0 | 4% |
| 1:2:1 | 52% |
| 1:2:2 | 66% |
| 1:2:3 | 74% |
| 1:2:4 | 84% |

TABLE 6b

| EPS:CaCl$_2$:HP-β-CD molar ratios | EPS in solution |
|---|---|
| 1:2:0 | 4% |
| 1:2:1 | 52% |
| 1:2:2 | 59% |
| 1:2:3 | 63% |
| 1:2:4 | 65% |

TABLE 6c

| EPS:CaCl$_2$: γ-CD molar ratios | EPS in solution |
|---|---|
| 1:2:0 | 4% |
| 1:2:1 | 41% |
| 1:2:2 | 51% |
| 1:2:3 | 57% |
| 1:2:4 | 62% |

EXAMPLE 7

To a solution in a pH 3.1 HCl/KCl buffer (I=0.1), containing about 1 mg/ml of Estramustine-17-phosphate disodium salt (EPS) and 4 mole of calcium chloride per mole of EPS, were added different quantities of cyclodextrins: β-cyclodextrin (β-CD), 2-hydroxypropyl-β-cyclodextrin (HP-β-CD) or γ-cyclodextrin (γ-CD), in order to have drug-:cyclodextrin molar ratios from 1:0 to 1:4 for evaluating the solubilization properties of cyclodextrins in dissolving a previously formed precipitate of EPS with calcium. The samples were filtered and the quantity of Estramustine-17-phosphate disodium salt in solution was assayed by UV spectroscopy.

The results are shown in Tables 7a, 7b and 7c.

TABLE 7a

| EPS:CaCl$_2$:β-CD molar ratios | EPS in solution |
|---|---|
| 1:4:0 | 4% |
| 1:4:1 | 50% |
| 1:4:2 | 64% |
| 1:4:3 | 69% |
| 1:4:4 | 79% |

TABLE 7b

| EPS:CaCl$_2$:HP-β-CD molar ratios | EPS in solution |
|---|---|
| 1:4:0 | 4% |
| 1:4:1 | 49% |
| 1:4:2 | 56% |
| 1:4:3 | 59% |
| 1:4:4 | 63% |

TABLE 7c

| EPS:CaCl$_2$:γ-CD molar ratios | EPS in solution |
|---|---|
| 1:4:0 | 4% |
| 1:4:1 | 45% |
| 1:4:2 | 50% |
| 1:4:3 | 55% |
| 1:4:4 | 61% |

EXAMPLE 8

A dissolution rate test has been performed comparing the performances of the already marketed, cyclodextrin-free, formulation of Estramustine-17-phosphate disodium salt, versus a formulation containing a molar ratio 1:2 of Estramustine-17-phosphate disodium salt: hydroxypropyl-β-cyclodextrin (EPS/HP-β-CD). The conditions were USP XXII No. 1 dissolution rate test (basket method) in sink conditions, 37° C., 100 r.p.m., HCl/KCl buffer pH 3.1 (I=0.1) with 1 mole of calcium chloride added in the dissolution medium per mole of drug. The results are shown in Table 8.

TABLE 8

| | Percent in solution | |
|---|---|---|
| Time (minutes) | EPS | EPS/HP-β-CD |
| 30 | 10.0 | 94 |

EXAMPLE 9

A dissolution rate test has been performed comparing the performances of various Estramustine-17-phosphate disodium salt (EPS) formulations containing different cyclodextrins: β-cyclodextrin (β-CD), 2-hydroxypropyl-β-cyclodextrin (HP-β-CD), γ-cyclodextrin (γ-CD) or dehydrated-β-cyclodextrin (de-β-CD) in a 1:2 molar ratio with the drug. The conditions were USP XXII No. 1 dissolution rate test (basket method) in sink conditions, 37° C., 100 r.p.m., HCl/KCl buffer pH 3.1 (I=0.1) with 1 mole of calcium chloride added in the dissolution medium per mole of drug.

The results are shown in Table 9.

TABLE 9

| | Percent in solution EPS:CD 1:2 molar ratio with | | | |
|---|---|---|---|---|
| Time (minutes) | β-CD | HP-β-CD | γ-CD | de-β-CD |
| 30 | 100 | 100 | 100 | 100 |

EXAMPLE 10

A dissolution rate test has been performed comparing the performances of various Estramustine-17-phosphate disodium salt (EPS) formulations containing different cyclodextrins: β-cyclodextrin (β-CD) or 2-hydroxypropyl-β-cyclodextrin (HP-β-CD) in a 1:2 molar ratio with the drug. The conditions were USP XXII No. 1 dissolution rate test (basket method) in sink conditions, 37° C., 100 r.p.m., phosphate buffer pH 6.8 (I=0.1) with 1 mole of calcium chloride added in the dissolution medium per mole of drug.

The results are shown in Table 10.

TABLE 10

| Time (minutes) | Percent in solution EPS:CD 1:2 molar ratio with | |
| --- | --- | --- |
| | β-CD | HP-β-CD |
| 30 | 93 | 100 |

EXAMPLE 11

A dissolution rate test has been performed comparing the performances of various Estramustine-17-phosphate disodium salt (EPS) formulations containing different cyclodextrins: β-cyclodextrin (β-CD) or 2-hydroxypropyl-β-cyclodextrin (HP-β-CD) in a 1:2 molar ratio with the drug. The conditions were USP XXII No. 1 dissolution rate test (basket method) in sink conditions, 37° C., 100 r.p.m., HCl/KCl buffer pH 3.1 (I=0.1) with 5 moles of calcium chloride added in the dissolution medium per mole of drug.

The results are shown in Table 11.

TABLE 11

| Time (minutes) | Percent in solution EPS:CD 1:2 molar ratio with | |
| --- | --- | --- |
| | β-CD | HP-β-CD |
| 30 | 100 | 100 |

We claim:

1. A pharmaceutical composition suitable for oral administration, comprising an estramustine compound and a cyclodextrin in a ratio from about 1:1 to 1:10, wherein said estramustine compound is selected from the group consisting of estramustine-17-phosphate and estramustine-17-phosphate disodium salt.

2. The pharmaceutical composition of claim 1, wherein the cyclodextrin is selected from the group consisting of α-cyclodextrin, β-cyclodextrin, γ-cyclodextrin, a partially etherified β-cyclodextrin, dehydrated cyclodextrin and dimethyl-β-cyclodextrin.

3. The pharmaceutical composition of claim 2, wherein the cyclodextrin is β-cyclodextrin.

4. The pharmaceutical composition of claim 2, wherein the cyclodextrin is hydroxypropyl-β-cyclodextrin.

5. The pharmaceutical composition of claim 2, wherein the cyclodextrin is γ-cyclodextrin.

6. The pharmaceutical composition of claim 2, wherein the cyclodextrin is a dehydrated cyclodextrin.

7. The pharmaceutical composition of claim 2, wherein the cyclodextrin is a partially etherified β-cyclodextrin.

8. The pharmaceutical composition of claim 1, which further contains a pharmaceutically acceptable carrier.

9. The pharmaceutical composition of claim 1, wherein said estramustine compound and said cyclodextrin are used in a ratio of from about 1:1 to 1:4.

10. The pharmaceutical composition of claim 1, which is in a solid, semi-solid or liquid form.

11. A method of inhibiting the precipitation of an estramustine compound in a gastrointestinal tract of a patient in need thereof, comprising administering the estramustine compound together with a cyclodextrin, said estramustine compound being selected from the group consisting of estramustine-17-phosphate and estramustine-17-phosphate disodium salt.

12. A method of treating a tumor, comprising administering to a patient in need thereof an effective amount of an estramustine compound and a cyclodextrin, said estramustine compound being selected from the group consisting of estramustine-17-phosphate and estramustine-17-phosphate disodium salt.

13. The method of claim 12, wherein said tumor is a prostate tumor.

* * * * *